United States Patent
Adelman

(10) Patent No.: US 6,983,915 B2
(45) Date of Patent: Jan. 10, 2006

(54) TRANSPORTABLE INTRAVENOUS BAG STAND

(76) Inventor: Gregg Z. Adelman, 333 N. Raleigh Farms Rd., Youngsville, NC (US) 27596

( * ) Notice: Subject to any disclaimer, the term of this patent is extended or adjusted under 35 U.S.C. 154(b) by 0 days.

(21) Appl. No.: 10/804,387

(22) Filed: Mar. 19, 2004

(65) Prior Publication Data

US 2004/0206862 A1  Oct. 21, 2004

Related U.S. Application Data

(60) Provisional application No. 60/463,695, filed on Apr. 17, 2003.

(51) Int. Cl.
*A47F 5/00* (2006.01)
(52) U.S. Cl. .............................. 248/125.8; 248/188.6; 248/188.7
(58) Field of Classification Search ............. 248/125.8, 248/188.5, 188.6, 188.7, 528, 150, 151, 157, 248/165, 167, 434, 435, 170, 171, 155.2, 248/155.3, 311.3; 211/196, 205, 85, 100, 211/171

See application file for complete search history.

(56) References Cited

U.S. PATENT DOCUMENTS

| 803,831 | A |   | 11/1905 | Krauth |
| 2,646,956 | A |   | 7/1953 | Cadwell et al. |
| 2,845,244 | A |   | 7/1958 | Prokop |
| 2,957,187 | A | * | 10/1960 | Raia .......................... 5/503.1 |
| 4,725,027 | A | * | 2/1988 | Bekanich ................. 248/125.8 |
| 4,744,536 | A |   | 5/1988 | Bancalari |
| 4,892,279 | A |   | 1/1990 | Lafferty et al. |
| 4,966,340 | A | * | 10/1990 | Hunter .................... 248/125.8 |
| 5,124,857 | A |   | 6/1992 | Pitz |
| 5,576,722 | A |   | 11/1996 | Bustillos |
| D390,952 | S |   | 2/1998 | Ward et al. |
| 5,772,162 | A | * | 6/1998 | Lin ............................ 248/121 |
| D457,239 | S |   | 5/2002 | Kunik |

* cited by examiner

*Primary Examiner*—Ramon O Ramirez
(74) *Attorney, Agent, or Firm*—McNair Law Firm, P.A.

(57) ABSTRACT

A transportable intravenous stand for carrying medical fluids, such as blood plasma or saline solutions, so as to allow the fluids to be gravity fed into a patient. This invention comprises a base, a collapsible support member, and a hanger member to allow for hanging fluid-dispensing containers. The base being collapsible and support member telescoping so as to provide for a compact, easily transportable stand for use in the field when providing medical treatment to a patient.

13 Claims, 4 Drawing Sheets

TRANSPORTABLE INTRAVENOUS BAG STAND

CROSS REFERENCE TO RELATED APPLICATION

This application claims priority from a provisional application filed Apr. 17, 2003 under Ser. No. 60/463,695 having the same title.

FIELD OF THE INVENTION

This invention is directed to a transportable intravenous bag stand for use in the field and more particularly to a transportable, collapsible intravenous stand having a collapsed position of less than 19 inches in height and an extended position of at least 50 inches in height.

BACKGROUND OF THE INVENTION

Unfortunately, medical treatment must be dispensed in the field in the event of traumatic events such as automobile accidents, airplane crashes, train collisions, workplace injury, and other such traumas. Specifically, emergency medical service (EMS) personnel, including firemen, respond to human injuries on a daily basis. It has been reported that over 40,000 EMS calls were responded to in Seattle, Wash. in the year 2000. Of these, over half of them required advanced life-saving techniques. The use of intravenous medication is significant and common for "in the field" medical treatment of physical trauma. However, the application of intravenous medication requires that the intravenous medication be delivered through a gravity fed system so that the intravenous medication bag must be gravitationally higher than the patient. Traditionally, the EMS personnel holds the bag higher than the patient to insure that the medication is being properly gravity fed. This requires that the EMS personnel, rather than performing other needed medical services, is required to simply hold an intravenous bag. This requirement wastes the resources of a valuable trained professional who would otherwise be providing much needed medical services. Alternatively, a non-EMS individual can be utilized to hold the intravenous bag while the EMS personnel provides medical services. However, this requires that a non-trained person crowd the patient while potentially life-saving medical services are being rendered. Therefore, providing a means for supporting an intravenous bag in a proper position without needlessly occupying EMS personnel and without crowding a patient with non-EMS personnel is a problem to which much attention should be directed.

Although intravenous supports are known, none are able to be used in the field due to the inability of these supports to be collapsible or be easily transportable. The EMS personnel carries equipment, typically, in a medical equipment bag that approximates 19 inches in length, 12 inches in width, and 8 inches in depth. As such, a collapsible, transportable intravenous stand that fits in EMS equipment bags is much needed for the medical industry and particularly for EMS personnel.

Previous intravenous stands simply cannot provide for this much needed application. For example, U.S. Pat. No. 4,832,294 provides for a T-shaped base, castor wheels, skid member and pole lacking telescoping features. Such a design cannot fit in EMS equipment bags. U.S. Pat. No. 4,629,074 shows a ceiling mounted "stand" and would not have application for "in the field" medical treatment. U.S. Pat. No. 4,905,944 requires a large base that is not suitable for easy transportation and cannot be practically contained in a medical equipment bag. U.S. Pat. No. 4,892,279 includes an interior cam-clutch section, pneumatic piston in the base, up to four intravenous hangers, negative inclined legs, double-wheeled castors, and movable hanger rods. This configuration simply makes this invention too bulky and too great a cross section to sufficiently be transported within an EMS equipment bag.

SUMMARY OF THE INVENTION

The advantages of this invention are achieved by providing a transportable intravenous bag stand comprising of a base support having a plurality of collapsible legs, a vertical support member extending generally upwards from said base support with at least one extension support member reasonably carried by the vertical support member to extend upwards from the vertical support member to a predetermined height, and, a c-shaped hanger member carried by the at least one extension support member for providing a means for hanging an intravenous bag from the hanger loop so that a transportable, collapsible intravenous bag stand is provided. The bag stand can include at least one bag support member carried by the at least one extension support member so that the intravenous bag hanging from the hanger member is displaced away from the at least one extension support member. The bag support member can be two downwardly extending arms arranged in opposed positions relative to the extension support member. Also the bag support member and the c-shaped hanger member can be integral. Further, the invention can include the base support that has three legs, a collapsed position where the bag stand is less than 19 inches, and an extended position where the bag stand is greater than 50 inches in length. The c-shaped hanger member can have a first end and a second end where the first end is vertically disposed above said second end so that the intravenous bag can be easily and securely placed upon the hanger member. Further, the vertical support member can have a first end and a second end where a plurality of legs are pivotally connected to the first end of the vertical support member and the positioning member is slidably carried by said vertical standard so as to be able to be disposed between the first end and the second end of the vertical standard, and at least one reinforcement member is carried by the plurality of legs and the positioning member so as to reinforce the stability of the base support. A combination lock and stop member integrated within at least one extension support member can allow the extension support member to be fixed in a particular position so as to provide for the desired height of the transportable intravenous bag stand and can prevent the at least one extension support member from releasing from the base support.

DETAILED DESCRIPTION OF THE PREFERRED EMBODIMENT

Figure 1:
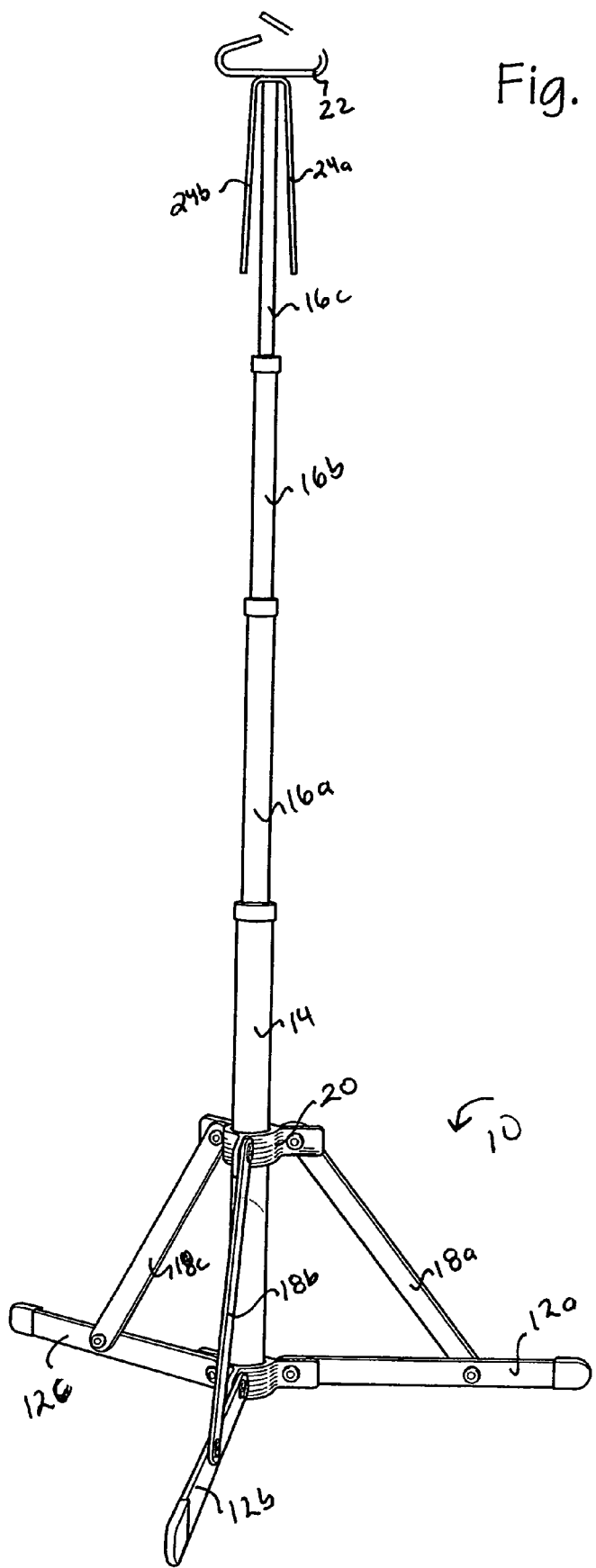
FIG. 1 is a perspective view of the invention.

Referring now to the figures, the preferred embodiment of the invention is described in more detail. Referring to FIG. 1, the transportable IV stand is shown in an open position. A base support, shown generally as 10, is shown having a plurality of legs, 12a through 12c. The three legs provide stable support, without being unduly cumbersome. The plurality of legs is connected to a vertical support member 14 having a first end and a second end. The plurality of legs is pivotally connected to the first end of vertical support member 14. This construction can also include a reverse tripod thereby minimizing the closed length, increasing the leg spread, and providing a lower center of gravity for greater stability. A plurality of extension support members 16a through 16c is telescopically carried by vertical support member 14. The extension members can be secured in a plurality of positions to provide for a plurality of heights. The extension members can be secured by a clutch look so that rotating one extension member inside disposed inside another extension member creates friction thereby securing the extension members. Further, a split collar configuration can be used to secure, with an operatively associated thumb screw, the extension members in a plurality of configurations for obtaining a plurality of heights. Further, a spring button configuration can be used to provide for predetermined setting of securing extension members to predetermined height settings. Reinforcement members, 18a through 18c, are pivotally connected to the plurality of legs and to a positioning member 20. The positioning member can be disposed near said first end of said second end of said vertical support member. In the preferred embodiment, the invention collapses to approximately a 16-inch length and can extend to approximately 50 inches in operation. Further, the invention has a weight of approximately 1.5 pounds to facilitate ease of transport, storage, and field use.

Figure 2:
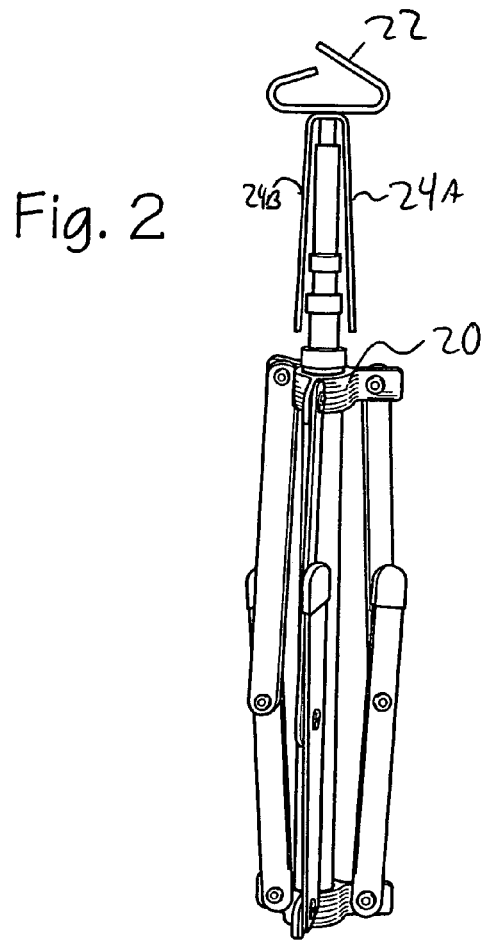
FIG. 2 is a perspective view of the invention.

A hanger 22 is carried by at least one extension support member for attaching an intravenous bag to the stand. Bag support members 24a and 24b are carried by the at least one extension support member so as to dispose the intravenous bag, hanging from the hanging member, away from the extension support members. The base support can be collapsed and the vertical support members and extension support members can telescope into each other to form a collapsed position as shown in FIG. 2.

Figure 3:
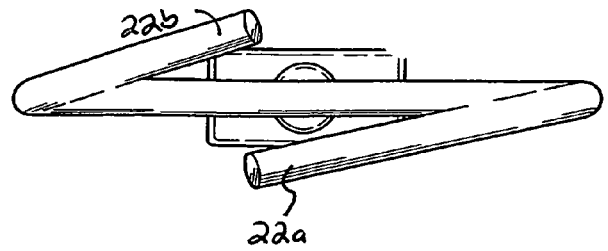
FIG. 3 is a top-down view of components of the invention.
Figure 4:
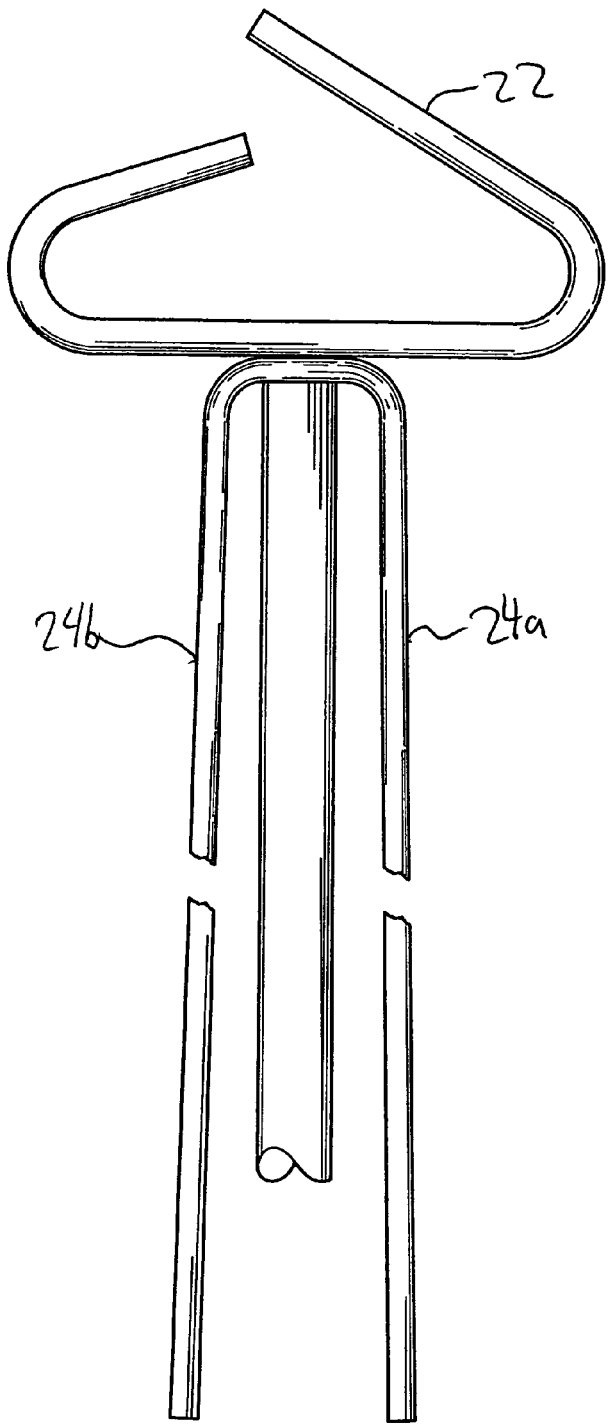
FIG. 4 is a frontal view of components of the invention.
Figure 5:
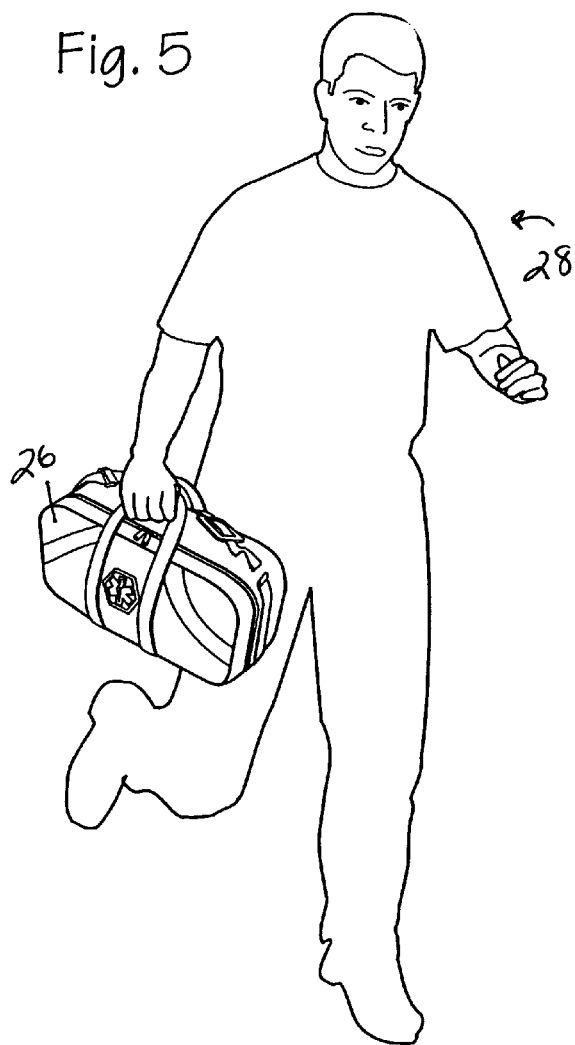
FIG. 5 is a perspective view of the invention being transported.

In the preferred embodiment, the hanging member can be a generally c-shaped member as shown in FIG. 3, with a first end, 22a and a second end, 22b. The first and second end of the hanging member can be offset so as to facilitate the placement of an intravenous bag on the hanging member. Further, the first end and second end of the hanging member can be vertically disposed away from each other to facilitate the placement of an intravenous bag on the hanging member as shown in FIG. 4. Further, the generally c-shaped member as shown in FIG. 3 protects the IV bag from falling off the stand during movement. The bag when placed on the c-shaped member can slide on with relative ease, however, in order for it to be removed it must be moved at an angle. Thus, it is unlikely that an intravenous bag would fall off of this c-shaped member during any movement. Also as shown in FIG. 4, the bag support members 24a and 24b disposed intravenous bag away from the extension support members. This is of tremendous benefit as there is no concern that the bag could be damaged by the extension support members. Further, if the bag stand is telescopically collapsed, the intravenous bags could remain on the c-shaped member without impeding the collapsing of the extension support members.

Figure 6:
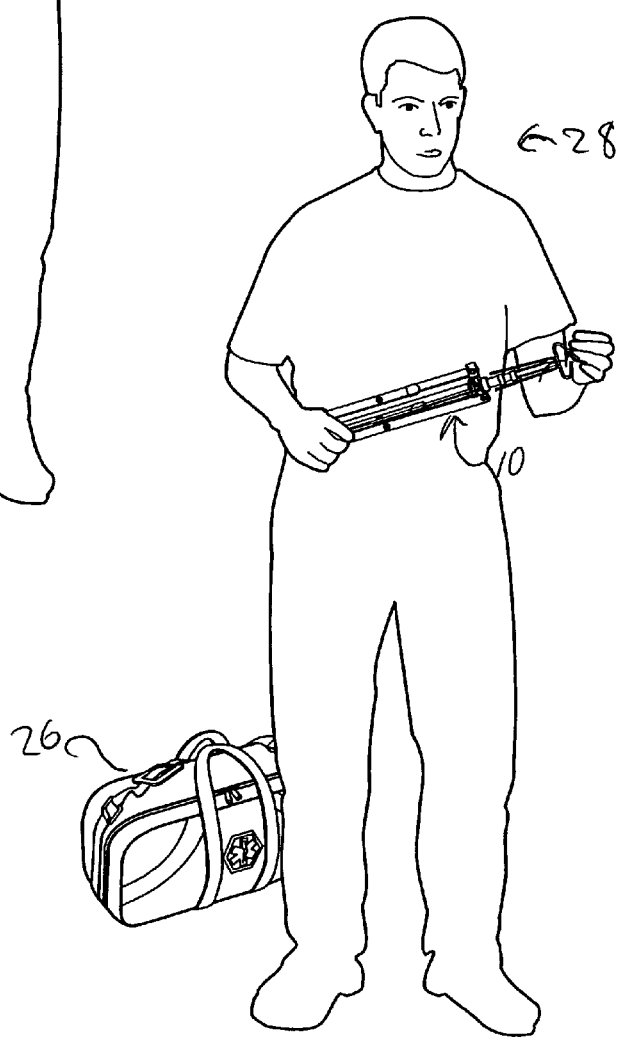
FIG. 6 is a perspective view of the invention being extended.
Figure 7:
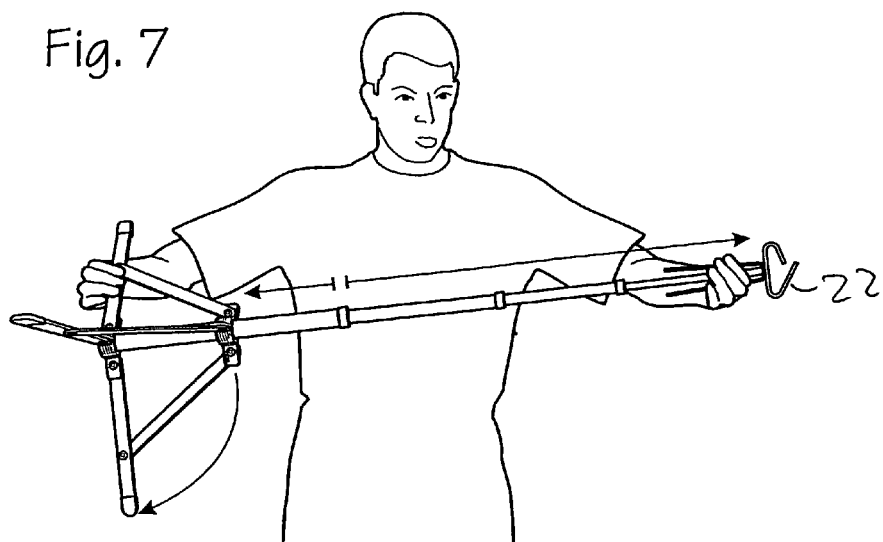
FIG. 7 is a perspective view of the invention being extended.
Figure 8:
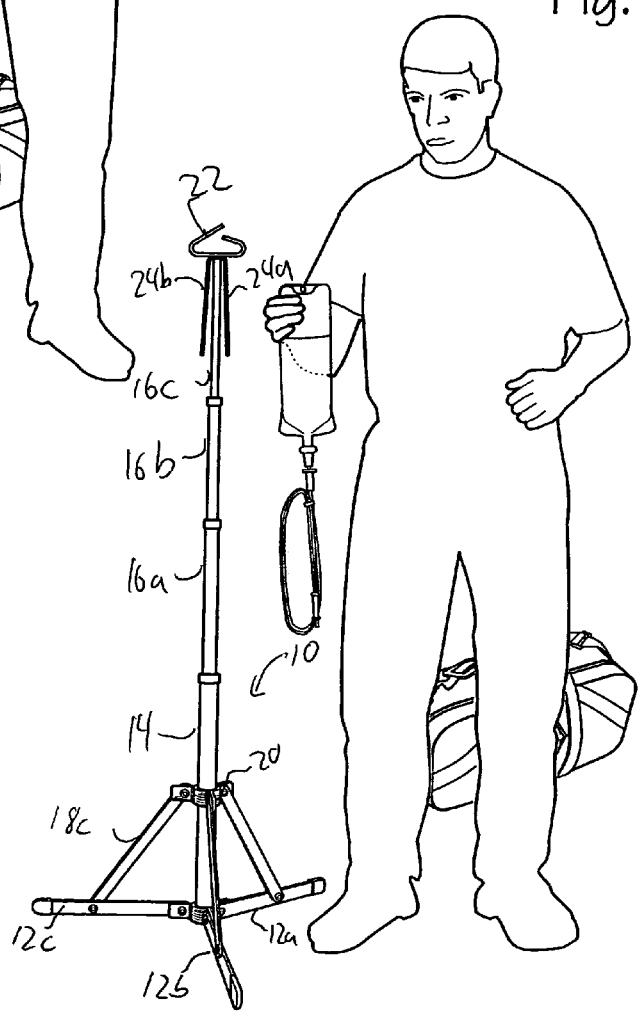
FIG. 8 is a perspective view of the invention being used.

In the use of the preferred embodiment, the intravenous stand can be placed into a medical bag 26 transported by EMS personnel, shown generally as 28. When retrieved from the bag as shown in FIG. 6, the collapsed position of the invention allows the EMS personnel to easily remove the invention from the EMS bag and extend the invention for medical treatment service as shown in FIG. 7. Once extended, the EMS personnel can place an intravenous bag on the stand for use in the field for "hands free" administration of intravenous medication to a patient.

What is claimed is:

1. A transportable intravenous bag stand comprising:
   a base support having a plurality of collapsible legs;
   a vertical support member extending generally upwards from said base support;
   at least one extension support member releaseably carried by said vertical support member to extend upwards from said vertical support member to a predetermined height;
   a c-shaped hanger member carried by said at least one extension support member for providing a means for hanging an intravenous bag;
   at least one bag support member carried by said at least one extension support member extending downwardly from said hanger member; whereby
   an associated intravenous bag hanging from said hanger member is engaged by and displaced away from said at least one extension support member by said bag support member and providing uninhibited movement of transportable, collapsible intravenous bag stand.

2. The transportable intravenous bag stand of claim 1 wherein said bag support member comprises two downwardly extending arms arranged in opposed positions relative to said extension support member.

3. The transportable intravenous bag stand of claim 1 wherein said bag support member and said c-shaped hanger member are integral.

4. The transportable intravenous bag stand of claim 1 wherein said base support includes three legs.

5. The transportable intravenous bag stand of claim 1 wherein said transportable intravenous bag stand has at least a first position and a second position wherein said transportable intravenous bag stand is less than 19 inches in length in said first position.

6. The transportable intravenous bag stand of claim 1 wherein said transportable intravenous bag stand has a first position and a second position wherein said transportable intravenous bag stand is greater than 49 inches in length in said second position.

7. The transportable intravenous bag stand of claim 1 wherein said c-shaped hanger member has a first end and a second end, wherein said first end is vertically disposed above said second end so that an intravenous bag can be easily and securely placed upon said hanger member.

8. The transportable intravenous bag stand of claim 1 wherein:
   said vertical support member has a first end and a second end;
   a plurality of legs pivotally connected to said first end of said vertical support member;
   a positioning member slideably carried by said vertical standard so as to be able to be disposed between said first end and said second end of said vertical standard; and, at least one reinforcement member carried by said plurality of legs and said positioning member so as to reinforce the stability of said base support.

9. The transportable intravenous bag of claim 1 including a combination lock and stop member integrated within at least one extension support member to allow said extension support member to be fixed in a particular position so as to provide for a desired height of said transportable intravenous bag stand and to prevent said at least one extension support member from releasing from said base support.

10. An improved transportable intravenous bag stand comprising:
   a plurality of permanently interconnected telescoping vertical support members including an outer telescoping vertical member each having a first end and a second end;
   a collapsible base having a plurality of legs permanently carried by said outer telescoping vertical support member;
   a hanger for supporting intravenous bags carried by an inner telescoping vertical support member;
   a plurality of combination lock and stop members integrated at said second end of a plurality of said telescoping vertical support members providing for a desired height of said transportable intravenous bag stand and permanently maintaining said telescoping vertical support members interconnected; and at least one bag support member carried at least one extension support member so that an associated intravenous bag hanging from said hanger member is displaced away from said at least one extension support member;
   a transportable intravenous bag stand having an expanded work position and a collapsed transport position is provided.

11. The transportable intravenous bag stand of claim 10 wherein said transportable intravenous bag stand has at least a first position and a second position wherein said transportable intravenous bag stand is less than 19 inches in length in said first position.

12. The transportable intravenous bag stand of claim 10 wherein said transportable intravenous bag stand has a first position and a second position wherein said transportable intravenous bag stand is greater than 49 inches in length in said second position.

13. The transportable intravenous bag stand of claim 10 wherein said hanger includes a c-shaped member having a first end and a second end, wherein said first end is vertically disposed above said second end so that an intravenous bag can be easily and securely placed upon said c-shaped member.

* * * * *